(12) United States Patent
Valadi

(10) Patent No.: US 11,006,661 B2
(45) Date of Patent: May 18, 2021

(54) CIGARETTE-LIKE DEVICE FOR ADMINISTRATION OF SUBSTANCES

(71) Applicant: Mamood Valadi, Taby (SE)

(72) Inventor: Mamood Valadi, Taby (SE)

(*) Notice: Subject to any disclaimer, the term of this patent is extended or adjusted under 35 U.S.C. 154(b) by 30 days.

(21) Appl. No.: 15/236,527

(22) Filed: Aug. 15, 2016

(65) Prior Publication Data

US 2018/0042292 A1 Feb. 15, 2018

(51) Int. Cl.
*A61M 15/06* (2006.01)
*A24D 1/00* (2020.01)
(Continued)

(52) U.S. Cl.
CPC ............ *A24D 1/002* (2013.01); *A24F 42/20* (2020.01); *A61M 11/04* (2013.01);
(Continued)

(58) Field of Classification Search
CPC .......... A22B 5/08; A22C 21/02; A24C 5/608; A24D 3/14; A24F 13/02; A24F 13/06; A24F 47/002; A24F 47/008; A24F 7/02; A61K 31/545; A61M 11/042; A61M 15/0016; A61M 15/0065; A61M 15/0068; A61M 15/0073; A61M 15/0091; A61M 15/0093; A61M 15/0096; A61M 15/06; A61M 2202/0468; A61M 2202/064; A61M 2205/3334; A61M 2205/581; A61M 2205/583; A61M 2205/8206; A61M 2209/045; A63F 7/386; B21D 22/022; B65B 55/02; B65B 55/08; C21D 1/26; C21D 1/673; C21D 1/74; C21D 1/78; C21D 9/67; C23C 2/02; C23C 2/06; C23C 2/28; C23C 2/40; E01C 23/088; E01C 2301/50;
(Continued)

(56) References Cited

U.S. PATENT DOCUMENTS 636,088 A * 10/1899 Voron
1,507,925 A * 9/1924 Marshall, Jr. .......... A24C 5/608
131/362
(Continued)

FOREIGN PATENT DOCUMENTS

WO 2006052177 5/2006

OTHER PUBLICATIONS

Thosar et al. "Antimicrobial efficacy of five essential oils against oral pathogens: An in vitro study",Eur J Dent. Sep. 2013; 7(Suppl 1): S71-S77. (Year: 2013).*

*Primary Examiner* — Annette Dixon
(74) *Attorney, Agent, or Firm* — Renner, Otto, Boisselle & Sklar, LLP

(57) ABSTRACT

A device comprising at least an outside surface which is intended to come into contact with the lips of the user during use, and wherein it is intended that the user shall inhale air drawn through the device. The device is coated with at least one first substance at least on a part of the outside surface intended to come into contact with the lips of the user, and the device includes at least one from the group consisting of a vaporizer for making an aerosol of solid particles of at least one second substance and/or liquid droplets of at least one second substance in air to be inhaled by the user, and a vaporizer for making a solution of at least one second substance in air to be inhaled by the user.

17 Claims, 2 Drawing Sheets

(51) Int. Cl.
*A24F 42/20* (2020.01)
*A61M 15/00* (2006.01)
*A61M 11/04* (2006.01)

(52) U.S. Cl.
CPC ...... *A61M 15/009* (2013.01); *A61M 15/0021* (2014.02); *A61M 15/06* (2013.01)

(58) Field of Classification Search
CPC ...... G01F 1/28; G03F 7/70033; G06M 1/041; G06M 1/163; G06M 1/241; H05B 2203/003; H05B 3/265; H05G 2/005; H05G 2/006; H05G 2/008; Y10T 428/12799
See application file for complete search history.

(56) References Cited

U.S. PATENT DOCUMENTS

| | | | | |
|---|---|---|---|---|
| 6,248,789 | B1* | 6/2001 | Weg | A61K 31/135 424/434 |
| 8,656,932 | B2 | 2/2014 | Valadi | |
| 2004/0211420 | A1* | 10/2004 | Minshull | A61M 15/0065 128/203.15 |
| 2004/0248964 | A1* | 12/2004 | Crooks | A61K 31/165 514/417 |
| 2010/0229881 | A1* | 9/2010 | Hearn | A24F 47/002 131/273 |
| 2014/0060554 | A1* | 3/2014 | Collett | H05B 3/265 131/328 |
| 2014/0123989 | A1* | 5/2014 | LaMothe | A24F 47/008 131/328 |
| 2015/0128969 | A1* | 5/2015 | Chapman | A24F 47/008 131/329 |
| 2015/0136158 | A1* | 5/2015 | Stevens | A24F 47/008 131/329 |
| 2015/0282527 | A1* | 10/2015 | Henry, Jr. | A24F 47/008 131/328 |
| 2015/0335074 | A1* | 11/2015 | Leung | A61M 15/06 131/328 |
| 2016/0007648 | A1* | 1/2016 | Sutton | A24F 7/02 131/187 |
| 2016/0135506 | A1* | 5/2016 | Sanchez | A24F 47/008 131/329 |
| 2016/0175257 | A1* | 6/2016 | Chandrasekaran | A61K 9/2886 424/465 |
| 2016/0271347 | A1* | 9/2016 | Raichman | A61M 15/06 |

* cited by examiner

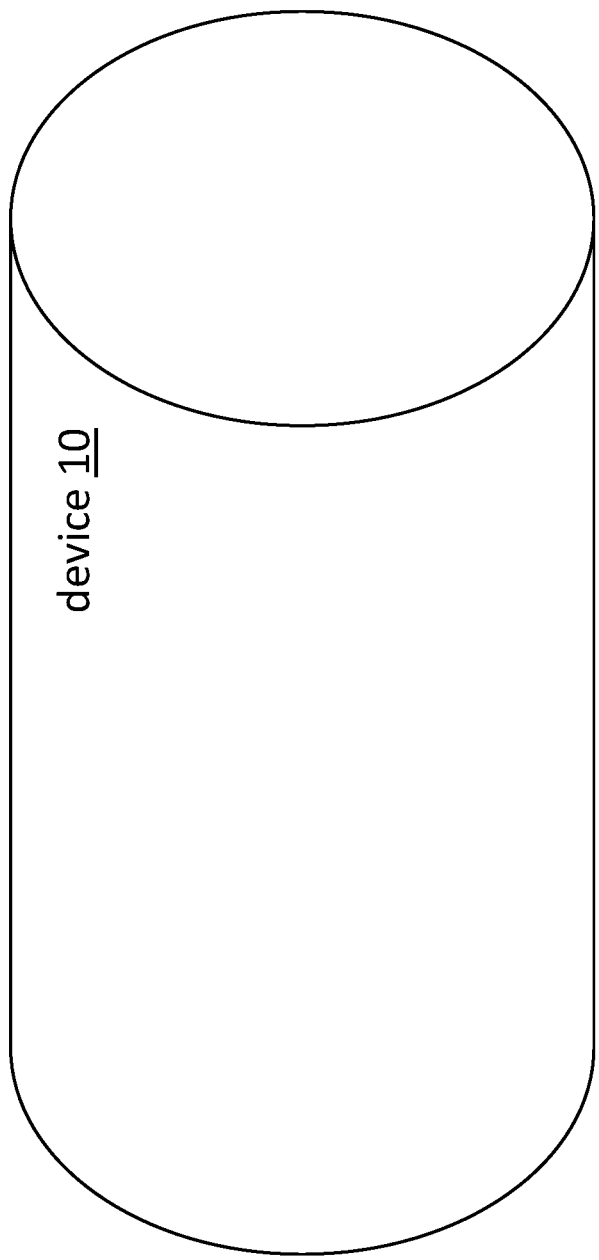

CIGARETTE-LIKE DEVICE FOR ADMINISTRATION OF SUBSTANCES

FIELD OF THE INVENTION

The present invention relates to a new cigarette-like device intended for administration of at least one substance to a human.

BACKGROUND

It is desired to replace ordinary cigarettes with healthier alternatives such as smokeless cigarettes and e-cigarettes and so on.

Further, it is desired to provide an efficient method of administering various substances to a human.

Cigarettes with nicotine on the outside are known.

WO2006052177 discloses a smokeless cigarette wherein a surface layer of the cigarette in at least a region at the part of the cigarette that when using the cigarette is intended to come in contact with the skin of a user, is impregnated with nicotine, so that the nicotine therein can be transferred to the skin of the user when handling and using the cigarette and therefrom into the blood system of the user.

There are also cigarettes, e-cigarettes and so on which administer nicotine via the air that is drawn through the device and inhaled by the user. The nicotine solution can be vaporized and inhaled.

U.S. Pat. No. 8,656,932 discloses a cigarette with nicotine on the sleeve and nicotine in a filter region.

SUMMARY OF THE PRESENT INVENTION

A problem in the state of the art regarding administration of various substances is that administration to the lips or via the inhaled air may not always be sufficient or may lead to undesired effects such as an unpleasant feeling on the lips.

Another problem in the art is that some substances to be administered may have an unpleasant taste and that masking the unpleasant taste with another substance which is administered the same route is difficult.

Advantages of the invention include the possibility of an easy way of administering various substance with the aid of a cigarette like object. Often a cigarette like object can be manufactured in a cost efficient way.

The administration of a substance using a single route may be difficult. For instance, the masking of an unpleasant taste can be easier when the substance and the aroma are administered by different routes. For instance, a substance can be vaporized and a tasteful substance can be administered via the lips.

Further, the administration of one or several substances can become more efficient with using both inhalation and contact with lips/fingers.

Before the invention is disclosed and described in detail, it is to be understood that this invention is not limited to particular configurations, process steps and materials disclosed herein as such configurations, process steps and materials may vary somewhat. It is also to be understood that the terminology employed herein is used for the purpose of describing particular embodiments only and is not intended to be limiting since the scope of the present invention is limited only by the appended claims and equivalents thereof.

It must be noted that, as used in this specification and the appended claims, the singular forms "a", "an" and "the" include plural referents unless the context clearly dictates otherwise.

BRIEF DESCRIPTION OF THE DRAWINGS

FIG. 2 is a diagrammatic illustration of the device according to another embodiment.

DETAILED DESCRIPTION OF THE PRESENT INVENTION

Figure 1A:
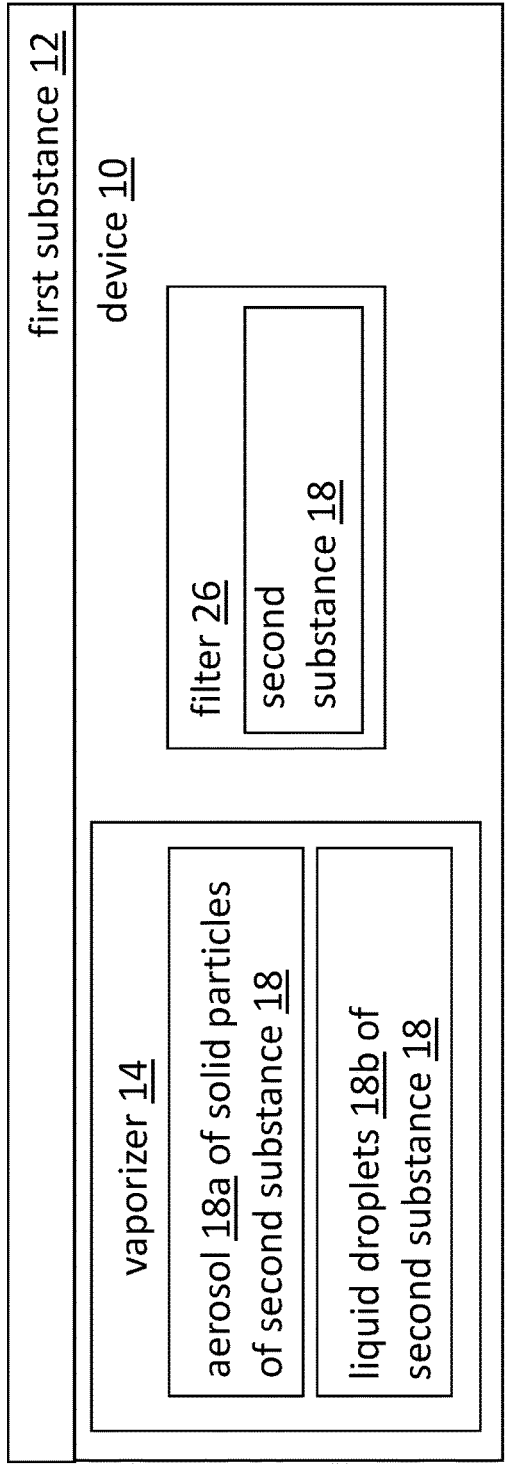
FIGS. 1a-1b are diagrammatic illustrations of the device according to various embodiments.
Figure 1B:
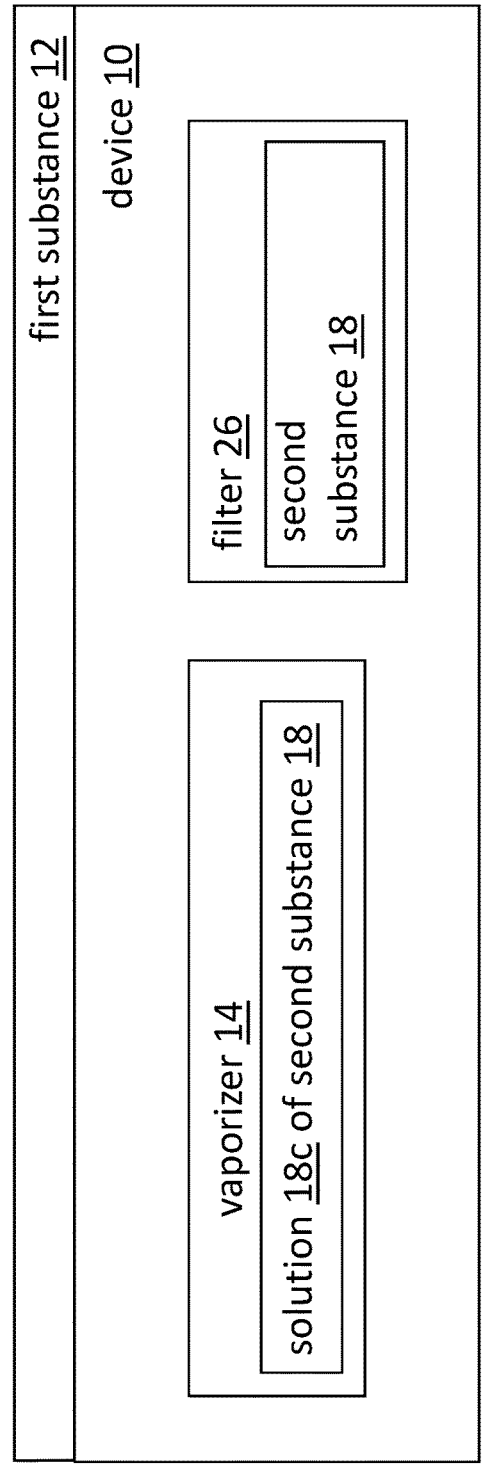

In a first aspect there is provided a device 10 intended to be used by a human user where at least a part of the outside surface of the device 10 is intended to come into contact with the lips and/or fingers of the user, and wherein it is intended that the user shall inhale air drawn through the device 10, wherein the device 10 is coated with at least one first substance 12 at least on a part of the outside surface intended to come into contact with the lips and/or fingers of the user, and that the device 10 comprises at least one from the group consisting of means (vaporizer 14) for making an aerosol 18a of solid particles of at least one second substance 18 and/or liquid droplets 18b of at least one substance 18 in air to be inhaled by the user, and means (vaporizer 14) for making a solution 18c of at least one second substance 18 in air to be inhaled by the user.

In one embodiment the device 10 comprises tobacco. In an alternative embodiment the device 10 comprises does not comprise tobacco.

In one embodiment the device 10 comprises a filter 26 impregnated with at least one substance 18.

In one embodiment the device 10 comprises a vaporizer.

In one embodiment the device 10 comprises at least one medical substance.

In one embodiment the device 10 comprises at least one substance intended to give a desired taste.

In one embodiment the at least one substance 12 at least on a part of the outside surface intended to come into contact with the lips and/or fingers of the user is at least one substance intended to give a desired taste.

In one embodiment the at least one substance 12 intended to give a desired taste is at least one selected from the group comprising whisky aroma, and cognac aroma.

In one embodiment the device 10 comprises at least one substance 18 selected from the group consisting of 4-Methylmethcathinone, a-Methylphenethylhydroxylamine, Acetyldihydrocodeine, Amphetamine, Cannabinol and derivatives, Cannabis, Codeine, Dihydrocodeine, Ethylmorphine, Glutethimide, Ketamine, Lefetamine, Lisdexamfetamine, Mecloqualone, Methaqualone, Methcathinone, Methoxetamine, Methylphenidate, Methylphenobarbitone, Naphyrone, Nicocodeine, Nicodicodine, Norcodeine, Pentazocine, Phenmetrazine, Pholcodine, Propiram, and Zipeprol.

In one embodiment the device 10 comprises at least one pharmaceutically active substance.

In one embodiment the device 10 comprises at least one pharmaceutically active substance.

In one embodiment the device 10 comprises at least one alkaloid.

In one embodiment the device 10 comprises at least one phenantrene.

In one embodiment the device 10 comprises at least one selected from the group consisting of morphine, codeine, and thebaine.

In one embodiment the device 10 comprises at least one selected from the group consisting of amphetamine, amphetamine derivatives, 3,4-Methylenedioxymethamphetamine, and ephedrine.

Any combination of two or more of all substances and classes of substances mentioned in the text as well as any other substance and substances and classes of substances can freely be combined to achieve desired effects in the present device.

In one embodiment the device 10 comprises at least one pharmaceutically acceptable adjuvant.

In one embodiment the device 10 is cylindrical.

In one embodiment the device 10 looks like a cigarette.

In one embodiment the device 10 is coated with at least one first substance 12 at least on a part of the outside surface intended to come into contact with the lips and/or fingers of the user, wherein the at least one first substance 12 has a pleasant taste, and wherein the device 10 comprises at least one second substance 18 with an unpleasant taste. In one embodiment the second substance 18 is intended to be inhaled as an aerosol 18*a*. The substance 12 which comes into contact with the lips of the user will mask the taste of the inhaled aerosol 18*a* which for some substances is more efficient compared to for instance a masking substance in the aerosol.

In one embodiment the at least one substance 12 is in liquid form.

In one embodiment the at least one substance 12 is in gel form.

In one embodiment the at least one substance 12 is present as a cream.

In one embodiment the at least one substance 12 is in solid form.

It is conceived that there is at least one substance 12 coated on at least a part of the outside surface of the device. Further there is at least one substance 18 from which an aerosol 18*a* and/or a solution 18*c* in air can be made. The least one substance 12 coated on at least a part of the outside surface of the device can be viewed as at least one first substance 12. The at least one substance 18 from which an aerosol 18*a* and/or a solution 18*c* in air is made can be viewed as at least one second substance 18. These two groups of substances can be the same or different substance.

The at least one second substance 18 is made into an aerosol 18*a* by means known to the skilled person. It can also be made into a solution 18*c* in air drawn through the device. The air comprising the aerosol 18*a* and/or solution 18*c* of substance in the air is intended to be inhaled by the user.

In one embodiment the device 10 comprises at least one vitamin.

In a second aspect there is provided a method of administrating at least one substance to a human characterized in that a device 10 described above is used.

The invention claimed is:

1. A device intended to be used by a human user where at least a part of the outside surface of the device is intended to come into contact with the lips of the user, and wherein it is intended that the user shall inhale air drawn through the device, wherein the device is coated with at least one first substance at least on a part of the outside surface intended to come into contact with the lips of the user, and the device comprises a vaporizer for making at least one of (i) an aerosol of solid particles of at least one second substance and/or liquid droplets of at least one second substance in air to be inhaled by the user, and (ii) a solution of at least one second substance in air to be inhaled by the user, wherein the at least one first substance is selected from the group consisting of 4-Methylmethcathinone, a-Methylphenethylhydroxylamine, Acetyldihydrocodeine, Amphetamine, Cannabinol and derivatives, *Cannabis*, Codeine, Dihydrocodeine, Ethylmorphine, Glutethimide, Ketamine, Lefetamine, Lisdexamfetamine, Mecloqualone, Methaqualone, Methcathinone, Methoxetamine, Methylphenidate, Methylphenobarbitone, Naphyrone, Nicocodeine, Nicodicodine, Norcodeine, Pentazocine, Phenmetrazine, Pholcodine, Propiram, and Zipeprol, and wherein the at least one second substance is selected from the group consisting of 4-Methylmethcathinone, a-Methylphenethylhydroxylamine, Acetyldihydrocodeine, Amphetamine, Cannabinol and derivatives, *Cannabis*, Codeine, Dihydrocodeine, Ethylmorphine, Glutethimide, Ketamine, Lefetamine, Lisdexamfetamine, Mecloqualone, Methaqualone, Methcathinone, Methoxetamine, Methylphenidate, Methylphenobarbitone, Naphyrone, Nicocodeine, Nicodicodine, Norcodeine, Pentazocine, Phenmetrazine, Pholcodine, Propiram, and Zipeprol.

2. The device according to claim 1, wherein the device comprises a filter impregnated with the at least one second substance.

3. The device according to claim 1, wherein the device comprises at least one alkaloid.

4. The device according to claim 1, wherein the device comprises at least one phenantrene.

5. The device according to claim 1, wherein the device comprises at least one selected from the group consisting of morphine, and thebaine.

6. The device according to claim 1, wherein the device comprises at least one selected from the group consisting of, amphetamine derivatives, 3,4-Methylenedioxymethamphetamine, and ephedrine.

7. The device according to claim 1, wherein the device comprises at least one pharmaceutically acceptable adjuvant.

8. The device according to claim 1, wherein the device is cylindrical.

9. The device according to claim 1, wherein the at least one first substance is in liquid form.

10. The device according to claim 1, wherein the at least one first substance is in gel form.

11. The device according to claim 1, wherein the at least one first substance is present as a cream.

12. The device according to claim 1, wherein the at least one first substance is in solid form.

13. The device according to claim 1, wherein the device comprises at least one vitamin.

14. The device according to claim 1, wherein the device further comprises tobacco.

15. The device according to claim 1, wherein the device additionally comprises at least one tasteable substance intended to give a desired taste.

16. The device according to claim 15 wherein the at least one tasteable substance intended to give a desired taste is at least one selected from the group consisting of whiskey aroma, and cognac aroma.

17. Method of administrating at least one substance to a human, wherein a device according to claim 1 is used.

* * * * *